United States Patent
Bombardelli et al.

(10) Patent No.: US 7,105,705 B2
(45) Date of Patent: Sep. 12, 2006

(54) HYPERFORIN DERIVATIVES, THE USE THEREOF AND FORMULATIONS CONTAINING THEM

(75) Inventors: Ezio Bombardelli, Milan (IT); Paolo Morazzoni, Milan (IT); Antonella Riva, Milan (IT); Nicola Fuzzati, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/512,067

(22) PCT Filed: Apr. 18, 2003

(86) PCT No.: PCT/EP03/04100

§ 371 (c)(1),
(2), (4) Date: Oct. 21, 2004

(87) PCT Pub. No.: WO03/091194

PCT Pub. Date: Jun. 11, 2003

(65) Prior Publication Data

US 2005/0165117 A1    Jul. 28, 2005

(30) Foreign Application Priority Data

Apr. 23, 2002    (IT)    .......................... MI2002A0872

(51) Int. Cl.
*C07C 49/00*    (2006.01)
*A61K 31/12*    (2006.01)

(52) U.S. Cl. ...................... 568/375; 568/377; 514/690; 514/732

(58) Field of Classification Search ................ 568/375, 568/377; 514/690, 732
See application file for complete search history.

(56) References Cited

U.S. PATENT DOCUMENTS 6,322,824 B1 * 11/2001 Chatterjee et al. .......... 424/730
6,444,662 B1 *  9/2002 Chatterjee et al. ..... 514/210.01
6,656,510 B1 * 12/2003 Bombardelli et al. ....... 424/730

FOREIGN PATENT DOCUMENTS

WO    WO 99/41220    8/1999
WO    WO 99/64388    12/1999

* cited by examiner

*Primary Examiner*—Sikarl A. Witherspoon
(74) *Attorney, Agent, or Firm*—Young & Thompson

(57) ABSTRACT

The use of the reduction products of hyperforin and adhyperforin, pharmaceutically acceptable salts or esters thereof, in the pharmaceutical and/or nutritional field, in particular in the treatment of depression and Alzheimer's disease.

14 Claims, No Drawings

HYPERFORIN DERIVATIVES, THE USE THEREOF AND FORMULATIONS CONTAINING THEM

FIELD OF THE INVENTION

The present invention relates to hyperforin and adhyperforin derivatives and the use thereof in the pharmaceutical and/or nutritional field, in particular in the treatment of depression and Alzheimer's disease.

TECHNOLOGICAL BACKGROUND

Flowering tops of *Hypericum perforatum* contain a number of classes of structurally different substances that act directly or indirectly on the central nervous system. The mechanisms of action of these compounds are different and comprise anti-MAO action (Suzuki O R. et al. Planta Med., 272–4, 1984), action on serotonin release and re-uptake (Muller W. E. et al Pharmacopsychiatry, 30, 102–107, 1997) and benzodiazepine-like activity (Coot J. M. Pharmacopsychiatry 30,108–112, 1997).

Hyperforin, a floroglucin derivative, is one of the main components of the lipophilic fraction of *Hypericum perforatum* flowering tops; said fraction also contains adhyperforin, a hyperforin higher homologue, although in lower concentration (Erdelmeier C. A. J., Pharmacopsychiatry, 31, 2–6, 1998).

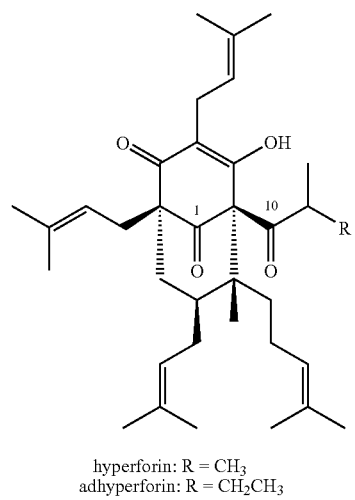

hyperforin: R = $CH_3$
adhyperforin: R = $CH_2CH_3$

Hyperforin has recently been the object of numerous studies that establish its important role as an antidepressant (Pharmacopsychiatry, 31 Suppl. 1, 1–60. 1998). Furthermore, it is recognized that the extracts of *Hypericum perforatum* can be used for the prophylaxis and treatment of neurodegenerative diseases, inter alia Alzheimer's disease (WO/9940905, WO0057707). In particular, hyperforin and adhyperforin salts with inorganic cations or ammonium salts were described for this purpose (WO9941220).

It is known from literature that hyperforin is poorly stable in the usual extraction and storage conditions; according to WO 97/13489, the hyperforin content in a St. John's Wort water-alcoholic extract falls already after a few weeks. WO 97/13489 further recites that, in order to obtain hyperforin stable extracts, antioxidants should be present during the whole work up (extraction, purification and storage). It is therefore evident that the high instability of hyperforin makes the preparation of hyperforin pharmaceutical formulations quite difficult. In order to obviate to said drawback, compounds more stable than hyperforin, such as the salts disclosed in WO 99/41220 and the hydroxy-functionalized derivatives (WO 99/64388) cited above, have recently been prepared.

It is moreover known (Bystrov et al., Bioorg. Khim, 1978) that hyperforin and adhyperforin can be transformed into the corresponding octahydroderivatives, octahydrohyperforin (Ia) and octahydroadhyperforin (Ib), by catalytic reduction of the isoprene side chains

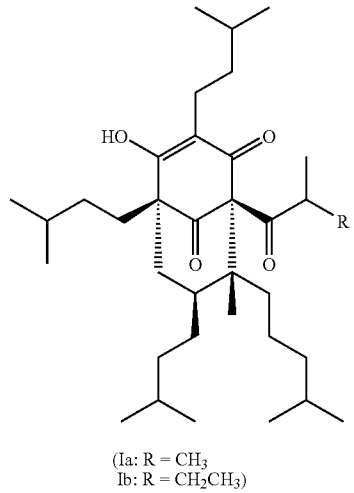

(Ia: R = $CH_3$
Ib: R = $CH_2CH_3$)

or into the corresponding tetrahydroderivatives, tetrahydrohyperforin (Ic) and tetrahydroadhyperforin (Id), by reduction of the keto groups at the 1- and 10-positions to hydroxy groups with metal hydrides.

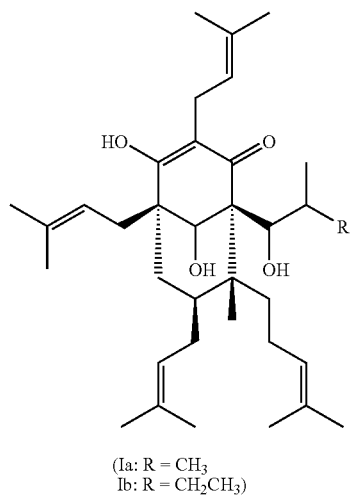

(Ia: R = $CH_3$
Ib: R = $CH_2CH_3$)

DETAILED DISCLOSURE OF THE INVENTION

It has now been found that hyperforin and adhyperforin derivatives obtainable by reduction of all double bonds of the isoprene chains and/or by reduction of the keto groups at the 1- and 10-positions to hydroxy groups not only have high stability, but also possess antidepressant, anxiolytic and anti-neurodegenerative activities surprisingly higher than hyperforin and adhyperforin.

Object of the present invention is therefore the use of hyperforin and adhyperforin derivatives of formula (I)

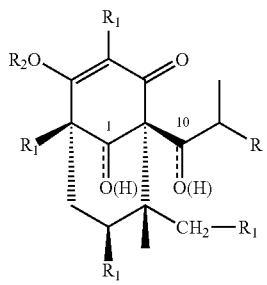

in which R is methyl or ethyl, $R_2$ is hydrogen, a pharmaceutically acceptable inorganic or organic base cation or a straight or branched $C_2$–$C_5$ acyl residue, and in which, alternatively:

a) $R_1$ is 3-methyl-but-1-yl and oxo groups are present at the 1- and 10-positions;

b) $R_1$ is 3-methyl-2-buten-1-yl and hydroxy groups are present at the 1- and 10-positions;

c) $R_1$ is 3-methyl-but-1-yl and hydroxy groups are present at the 1- and 10-positions.

for the preparation of medicaments, in particular for the preparation of medicaments for the treatment of depression and Alzheimer's disease.

Preferred compounds of formula (I) as defined at a) are those in which $R_2$ is hydrogen, in the following defined octahydrohyperforin (Ia) and octahydroadhyperforin (Ib):

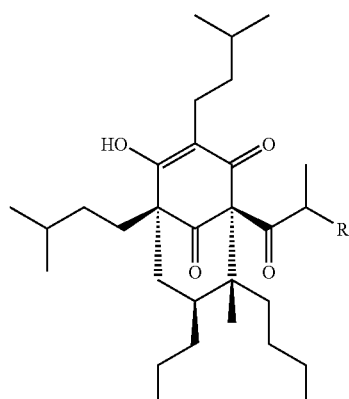

(Ia: R = CH$_3$
Ib: R = CH$_2$CH$_3$)

Preferred compounds of formula (I) as defined at b) are those in which $R_2$ is hydrogen (in the following defined tetrahydrohyperforin Ic and tetrahydroadhyperforin Id), tetrahydrohyperforin (Ic) being most preferred:

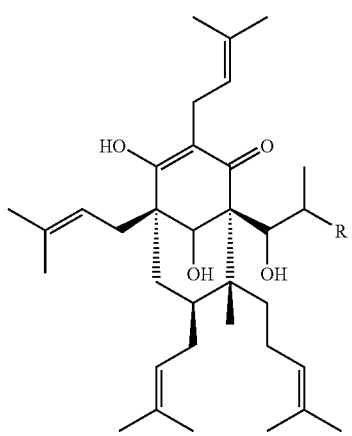

(Ic: R = CH$_3$
Id: R = CH$_2$CH$_3$)

Preferred compounds of formula (I) as defined at c) are those in which R2 is hydrogen (in the following defined dodecahydrohyperforin Ie and dodecahydroadhyperforin If), dodecahydrohyperforin (Ie):

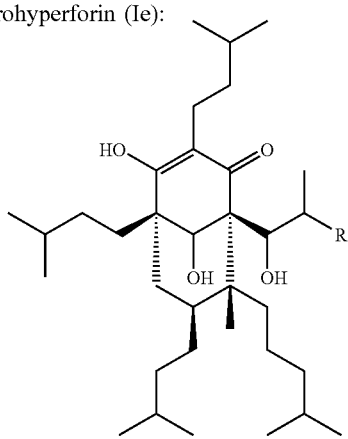

(Ie): R = CH$_3$
(If): R = CH$_2$CH$_3$

Further preferred compounds of formula (I) as defined at a) are those in which $R_2$ is lithium (octahydrohyperforin lithium salt Ig and octahydroadhyperforin lithium salt Ih), octahydrohyperforin lithium salt (Ig) tetrahydrohyperforin (Ic) being most preferred:

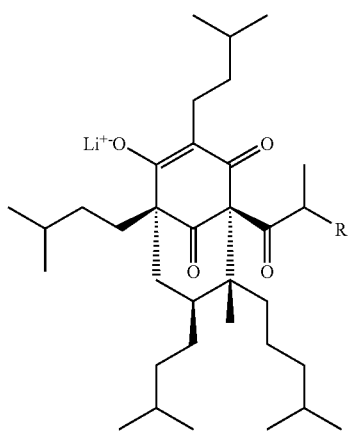

(Ig: R = CH$_3$
Ih: R = CH$_2$CH$_3$)

Further preferred compounds of formula (I) as defined at a) are those in which $R_2$ is acetyl (acetyloctahydrohyperforin Ii and acetyloctahydroadhyperforin Il), acetyloctahydrohyperforin (Ii) tetrahydrohyperforin (Ic) being most preferred:

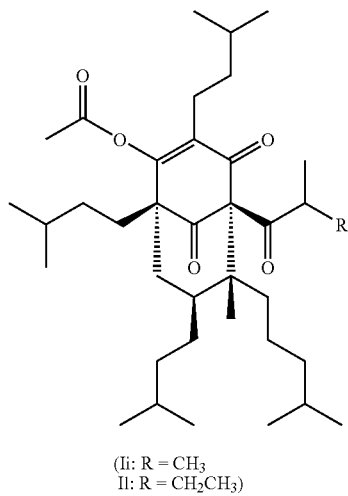

(Ii: R = CH$_3$
Il: R = CH$_2$CH$_3$)

Dodecahydrohyperforin (Ie), dodecahydroadhyperforin (If), acetyloctahydrohyperforin (Ii) and acetyloctahydroadhyperforin (Il) are novel compounds and are also part of the present invention.

The compounds of formula (Ia) and (Ib) are obtained through reduction of the isoprene side chains by catalytic hydrogenation, using for example palladium on charcoal or Nickel/Raney.

The compounds of formula (Ic) and (Id) are obtained by reduction of the keto groups at the 1- and 10-positions with hydrides, selected for example from NaBH$_4$, Redal®, Vitride®, LiAlH$_4$.

The compounds of formula (Ie) and (If) are obtained by reducing first the isoprene side chains and then the keto groups at the 1- and 10-positions according to what described above.

Compounds of formula (I) in which $R_2$ is an inorganic or organic base cation or an acyl residue, can be prepared from compounds of formula (I) in which $R_2$ is hydrogen by salification or esterification with conventional methods.

The process for the preparation of the compounds of the invention starting from the flowering tops of *Hypericum perforatum* can be summarized as follows:

The flowering tops of *Hypericum perforatum* can be extracted with alcohols or aliphatic ketones, either pure or in a mixture thereof with water or with gas in supercritical conditions; the resulting extract is partitioned between n-hexane and aqueous solutions of aliphatic alcohols. The hexane solution is extracted with alkaline methanol to extract hyperforin and adhyperforin. The methanolic solution is acidified, then treated with a weakly basic ion exchange resin, which selectively retains hyperforin and adhyperforin. The resin is eluted with acidic methanol and the eluate is concentrated to small volume, then diluted with water and back-extracted with n-hexane. The hexane solution is concentrated to small volume and the resulting concentrate is ready for derivatization. The residue is taken up in chlorinated solvents and the suitable reactive is added thereto, according to the procedures reported in the examples.

The compounds of the invention have shown antidepressant effect, which was evaluated in the rat by the forced swimming test, evaluating the parameters: struggling, floating and swimming according to what described by Cervo et al. in Neuropharmacology, 26, 14969–72, 1987. The compounds were administered in 3 doses: 30 minutes after the pre-test, 5 hours and 30 minutes before the test. The results reported in the table below prove that the compounds of the invention are more active than parent hyperforin.

| Treatment | mg/Kg | Struggling (sec.) | Floating (sec.) | Swimming (sec.) |
|---|---|---|---|---|
| Carrier | | 7.0 ± 2.4 | 174.5 ± 15.9 | 118.5 ± 15.8 |
| Octahydrohyperforin lithium salt | 6.25 | 63.1 ± 5.8 | 59.5 ± 11.3 | 177.4 ± 14.9 |
| Tetrahydrohyperforin | 6.25 | 51.4 ± 4.1 | 68.4 ± 7.6 | 193.4 ± 13.2 |
| Dodecahydrohyperforin | 6.25 | 62.13 ± 5.1 | 55.1 ± 6.2 | 169.5 ± 10.1 |
| Acetyloctahydrohyperforin | 6.25 | 73.9 ± 5.9 | 68.4 ± 5.7 | 171.9 ± 11.4 |
| Hyperforin | 6.25 | 30.4 ± 4.6 | 60.4 ± 7.3 | 99.3 ± 10.6 |
| Desipramin | 10 | 148.3 ± 12.6 | 53.0 ± 9.2 | 98.8 ± 7.9 |

The compounds of the invention also proved particularly active against Alzheimer's disease, due to their ability to increase APPs, the soluble, harmless form of Alzheimer Precursor Protein (APP). It is in fact known that proteolytic cleavage of Alzheimer Precursor Protein (APP) is mediated both by β- and γ-secretase, inducing an increased production of amyloid peptide Ab1-42 (which also plays a central role in the appearance of Alzheimer's disease), and α-secretase, giving raise to soluble APPs which have no pathogenic activity (Eslr W. P., Wolfe M. S., Science, 293, 1449–54, 2001).

The effect of the compounds of the invention on the release of APPs produced by α-secretase was evaluated in the culture medium of a neuroblastoma cell line (SH-SY5Y) according to the procedure described by Galbete J. L. et al. in Biochem J. 348,307–313, 2000.

The results reported in the following table show that the tested compounds activate α-secretase-mediated APP metabolism, inducing an increase in APPs secreted in the culture medium:

| | APPs % |
|---|---|
| Controls | 100 |
| 10 μM Hyperforin | 296 |
| 10 μM Octahydrohyperforin Lithium Salt | 1383 |

-continued

| | APPs % |
|---|---|
| 10 µM Tetrahydrohyperforin | 926 |
| 10 µM Dodecahydrohyperforin | 879 |
| 10 µM Acetyloctahydrohyperforin | 954 |

The compounds of the invention can be formulated according to conventional techniques, for example according to what described in Remington's Pharmaceutical Sciences Handbook, XVII Ed. Mack Pub., N.Y., U.S.A, in the form of soft-gelatin capsules, hard-gelatin capsules, tablets, suppositories; preferably the extract of the invention is formulated in soft-gelatin capsules or in controlled-release formulations. The dosage ranges from 10 to 100 mg per unit dose in the usual formulations and up to 200 mg in the controlled-release formulations, in this case the suggested dose being 200 mg per dose/daily. Furthermore, the compounds can be administered through the controlled-release transdermal route applying the formulation in the proximal area to the cerebral carotid artery derivations. The dosages of compound in these formulations range from 10 to 100 mg per dose/daily.

The examples reported hereinbelow illustrate the invention in greater detail.

EXAMPLES

Example 1

Preparation of Hyperforin 10 kg of flowering tops of *Hypericum perforatum* and 30 L of methanol are extracted in a 50 L extraction plant and the mass is left to stand at room temperature for 3 hrs; the extraction is repeated 3 more times, then the combined extracts are concentrated under vacuum to 5 kg and the concentrate is extracted with 3×5 L of hexane. The water-methanol solution is discarded, while the hexane one is back-extracted with alkali methanol (KOH) until exhaustion of hyperforin and adhyperforin.

This solution is neutralized and filtered through a weakly basic Amberlite resin, which selectively retains hyperforin and adhyperforin; the retained product is eluted again with methanol acidified with phosphoric acid; the methanolic eluate is concentrated under vacuum at 25° C., the diluted water and back-extracted with n-hexane until exhaustion of of hyperforin.

The combined organic layers are decolourized with 0.3% charcoal, then dried over $Na_2SO_4$ and concentrated to an oil below 40° C. under vacuum. After solidification the oil yelds a wax (0.52 kg) containing approx. 90% of hyperforin.

Example 2

Preparation of Octahydrohyperforin Dicyclohexylammonium Salt 50 g of hyperforin obtained as described in Example 1 are dissolved in 500 ml of ethyl acetate in the presence of 2 g of 5% palladium on charcoal and hydrogenated until complete hydrogen absorption. The catalyst is filtered off, the solution is concentrated to dryness under vacuum and the residue is dissolved in n-hexane. The solution is added with a stoichiometric amount of dicyclohexylamine, to obtain a sufficiently selective crystallization of the corresponding salt.

62 g of octahydrohyperforin dicyclohexylammonium salt are obtained, having the following spectroscopical characteristics:

$^1$H-NMR (300 MHz $CDCl_3$): δ 3.03 (2H, m, CH-DCHA), 2.55–2.30, 2.10–1.76 (20H, m, $CH_2$-DCHA), 1.70–1.10 (22H, m, H-4, H-11, $CH_2$-5, $CH_2$-15, $CH_2$-16, $CH_2$-17, $CH_2$-21, $CH_2$-22, $CH_2$-26, $CH_2$-27, $CH_2$-31, $CH_2$-32), 0.97–0.83(24H, d, $CH_3$-19, $CH_3$-20, $CH_3$-24, $CH_3$-25, $CH_3$-29, $CH_3$-30, $CH_3$-34, $CH_3$-35), 1.19, 1.12 (6H, d, J=6.5 Hz, $CH_3$-12, $CH_3$-13), 0.91 (3H, s, $CH_3$-14).

$^{13}$C-NMR (75 MHz $CDCl_3$): δ 213.1, 211.1, 186.3, 183.6 119.0, 82.5, 60.8, 53.5, 47.5, 44.2, 41.3, 41.0, 40.9, 38.2, 38.1, 37.8, 33.8, 31.0, 30.7, 30.0, 29.4, 28.8, 28.3, 27.9, 27.1, 25.4, 25.1, 24.9, 23.5, 23.2, 23.1, 22.9, 22.8, 22.7, 22.5, 13.7. ESIMS m/z 567 [M+Na$^+$] (100), 1111 [2M+Na$^+$] (91).

Example 3

Preparation of Tetrahydrohyperforin 2 g of hyperforin (M. W. =536,01) are dissolved in 20 ml of THF under magnetic stirring; the solution is added with $LiAlH_4$ in strong excess (1 g, 0.026 mol, M. W.=38). The progress of the reaction is monitored by TLC (eluent petroleum ether/EtOAc 9:1). After ten minutes the reaction is completed.

$Na_2S_2O_4$.10$H_2O$ supported on Celite (3:1 by weight) is added to destroy the reactive excess: the reaction is highly exothermic, therefore it should be cooled with ice. Part of the solvent evaporates due to the developed heat. The mixture is filtered through Celite and the filtrate is washed three times with 20 ml of AcOEt. The solution is placed in a 150 ml round-bottom necked flask and the solvent is evaporated off completely.

The resulting mixture is purified by column chromatography, using a 200 ml column packed with 100 ml of silica gel and petroleum ether/EtOAc 95:5 as eluent mixture. Eluate fractions of approx. 20 ml are collected and the content is checked by TLC (petroleum ether/EtOAc 9:1). The more abundant product (1.5 g), crystallized from methanol has the following spectroscopical properties:

$^1$H-NMR (300 MHz $CDCl_3$): δ 5.11 (1H, m, H-22), 5.00 (3H, m, H-17, H-27, H-32), 3.11 (1H, dd, J=14.0, 7.4 Hz, $CH_2$-26), 2.92 (1H, dd, J=14.0, 7.0 Hz, $CH_2$-26), 2.50–1.35 (12H, m, H-4, H-11, $CH_2$-5, $CH_2$-15, $CH_2$-16, $CH_2$-21, $CH_2$-31), 1.80–1.52 (24H, s, $CH_3$-19, $CH_3$-20, $CH_3$-24, $CH_3$25, $CH_3$-29, $CH_3$-30, $CH_3$-34, $CH_3$-35), 1.19–0.95 (9H, d, $CH_3$-12, $CH_3$-13, $CH_3$-14).

$^{13}$C-NMR (75 MHz $CDCl_3$): δ 200.5, 174.3, 134.1, 132.6, 131.2 130.6, 125.8, 123.9, 122.6, 120.5, 119.4, 79.2, 73.1, 39.6, 37.2, 30.5, 32.8, 31.3, 30.2, 26.1, 26.0, 25.8, 23.5, 23.1, 21.9, 20.0, 18.3, 18.1, 17.8, 15.6.

ESIMS m/z 1103 [2M+Na$^+$] (100), 541 [M+H$^+$] (25), 563 [M+Na$^+$] (12)

Example 4

Preparation of Octahydroadhyperforin Lithium Salt 15 g of octahydrohyperforin dicyclohexylammonium salt are eluted on an acidic resin (Dowex 50×8, 300 g) with 600 ml of methanol. 11.01 g of octahydrohyperforin are obtained, which are added with 0.8745 g of LiOH monohydrate dissolved in water. The mixture is evaporated to dryness to obtain 11.41 g of lithium salt having the following spectroscopical characteristics:

$^1$H-NMR (300 MHz $CDCl_3$): δ 1.93–1.00 (22H, m, H-4, H-11, $CH_2$-5, $CH_2$-15, $CH_2$-16, $CH_2$-17, $CH_2$-21, $CH_2$-22, $CH_2$-26, $CH_2$-27, $CH_2$-31, $CH_2$-32), 1.00–0.80 (24H, d, $CH_3$-19, $CH_3$-20, $CH_3$-24, $CH_3$-25, $CH_3$-29, $CH_3$-30, $CH_3$-34, $CH_3$-35), 1.20, 1.06 (6H, d, J=6.3 Hz, $CH_3$-12, $CH_3$-13 ), 0.91(3H, s, $CH_3$-14).

$^{13}$C-NMR (75 MHz CDCl$_3$): δ 211.4, 191.3, 184.6, 82.7, 61.5, 51.3, 47.7, 41.5, 40.5, 38.2, 37.9, 37.7, 33.9, 30.5, 29.6, 28.7, 28.3, 28.1, 27.1, 23.3, 23.1, 23.0, 22.8, 22.7, 22.4, 22.0, 14.0.

ESIMS m/z 551 [M+H$^+$] (100), 557 [M+Li$^+$] (40), 1102 [2M+H$^+$] (71), 1108 [M+Li$^+$] (75).

Example 5

Preparation of Dodecahydrohyperforin 1.72 g of dicyclohexylammonium octahydrohyperforinate (M.W.=716; 2,41 mmol) are dissolved in 20 ml of THF, under magnetic stirring; the solution is added with a strong excess (3.5 g) of LiAlH$_4$ (M. W.=38; 0.092 mol). The progress of the reaction is monitored by TLC (eluent petroleum ether/EtOAc 9: 1). After ten minutes the reaction is completed.

The reactive excess is destroyed as described in example 5. The mixture is filtered and the residue is thoroughly washed with ethyl acetate. The solution is evaporated to dryness, the reaction crude is dissolved in 15 ml of petroleum ether/ethyl ether 3:1 and the solution is placed in a 150 ml separatory funnel. The organic phase is washed three times with 2N sulfuric acid and subsequently with brine. The aqueous phase is discarded, the organic one is dried over Na$_2$SO$_4$ and concentrated to dryness. The resulting product is purified by column chromatography on 75 g of silica gel, eluting the desired compound with petroleum ether/ethyl acetate 99:1. 0.9 g of dodecahydrohyperforin are obtained, having the following spectroscopical characteristics:

EIMS m/z 548 [M]$^+$.

Example 6

Preparation of Acetyloctahydrohyperforin 300 mg of acetylhyperforin (M.W.=578; 0.52 mmol) are dissolved in 3 ml of MeOH in a two-necked round-bottom flask, then the catalyst (5% Pd on charcoal) is added. The reaction is monitored by TLC (petroleum ether/EtOAc 95:5 Rfp=0.43; Rfa=0.52). After four hours the reaction is completed. The catalyst is filtered off through a layer of Celite, then methanol is evaporated off.

The reaction product is purified by column chromatography on 30 g of silica gel, eluting with a petroleum ether/ethyl acetate 9:1 mixture. Crystallization from methanol affords 150 mg of the desired compound having the following spectroscopical characteristics:

EIMS m/z 586 [M]$^+$.

The invention claimed is:

1. A hyperforin and adhyperforin derivative of formula (I)

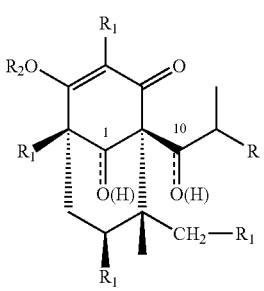

(I)

in which R is methyl or ethyl, R$_2$ is hydrogen, a pharmaceutically acceptable inorganic or organic base cation or a straight or branched C$_2$–C$_5$ acyl residue, and in which, alternatively:

a) R$_1$ is 3-methyl-but-1-yl and oxo groups are present at the 1- and 10-positions;

b) R$_1$ is 3-methyl-2-buten-1-yl and hydroxy groups are present at the 1- and 10-positions;

c) R$_1$ is 3-methyl-but-1-yl and hydroxy groups are present at the 1- and 10-positions.

2. The derivative as claimed in claim 1 for the preparation of medicaments for use in the treatment of depression and Alzheimer's disease.

3. The derivative as claimed in claim 1 in which R$_2$ is hydrogen.

4. A hyperforin and adhyperforin derivative of formula (I)

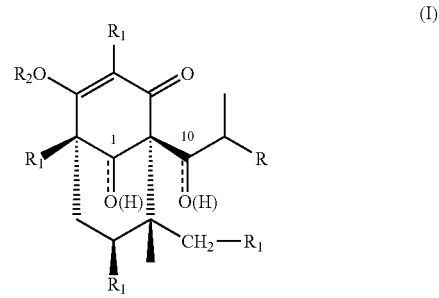

(I)

in which R is methyl or ethyl, R$_2$ is hydrogen, a pharmaceutically acceptable inorganic or organic base cation or a straight or branched C$_2$–C$_5$ acyl residue, and in which, alternatively:

a) R$_1$ is 3-methyl-but-1-yl and oxo groups are present at the 1 and 10-positions;

b) R$_1$ is 3-methyl-2-buten-1-yl and hydroxy groups are present at the 1- and 10-positions;

c) R$_1$ is 3-methyl-but-1-yl and hydroxy groups are present at the 1- and 10-positions, in which R$_2$ is lithium, R$_1$ is 3-methyl-but-1-yl and oxo groups are present at the 1- and 10-positions.

5. The derivative as claimed in claim 4 in which R is methyl.

6. The derivative as claimed in claim 1 in which R$_2$ is acetyl, R$_1$ is 3-methyl-but-1-yl and oxo groups are present at the 1- and 10-positions.

7. The derivative as claimed in claim 6 in which R is methyl.

8. A compound selected from:
dodecahydrohyperforin (Ie), dodecahydroadhyperforin (If),
acetyloctahydrohyperforin (Ih) and
acetyloctahydroadhyperforin (Ii).

9. A pharmaceutical composition containing the compound according to claim 4.

10. The compound according to claim 8, wherein said compound is dodecahydrohyperforin (Ie).

11. The compound according to claim 8, wherein said compound is dodecahydroadhyperforin (If).

12. The compound according to claim 8, wherein said compound is acetyloctahydrohyperforin (Ih).

13. The compound according to claim 8, wherein said compound is acetyloctahydroadhyperforin (Ii).

14. A pharmaceutical composition containing the compound according to claim 1.

* * * * *